(12) United States Patent
Wong et al.

(10) Patent No.: US 6,872,824 B2
(45) Date of Patent: Mar. 29, 2005

(54) PYRIMIDINE SPIROBIFLUORENE OLIGOMER FOR ORGANIC LIGHT-EMITTING DEVICE

(75) Inventors: Ken Tsung Wong, Lujhou (TW); Yuan Li Liao, Tzu Tung Hsiang (TW); Chung Chih Wu, Taipei (TW); Yu Ting Lin, Wufong Township, Taichung County (TW); Huo Hsien Chiang, Taipei (TW)

(73) Assignee: Echem Hightech Co., Ltd., Hsinchu Hsien (TW)

( * ) Notice: Subject to any disclaimer, the term of this patent is extended or adjusted under 35 U.S.C. 154(b) by 0 days.

(21) Appl. No.: 10/759,046

(22) Filed: Jan. 20, 2004

(65) Prior Publication Data

US 2004/0147742 A1 Jul. 29, 2004

(30) Foreign Application Priority Data

Jan. 21, 2003 (TW) ........................................ 92101646 A

(51) Int. Cl.$^7$ ............................................... C07D 403/02
(52) U.S. Cl. ........................................ 544/294; 313/506
(58) Field of Search .......................................... 544/294

(56) References Cited

PUBLICATIONS

Wu et al., Highly bright blue organic light–emitting devices using spirofluorene–cored conjugated compounds, Applied Physics Letters, vol. 81, No. 4, pp. 577–579, Jul. 2002.*

* cited by examiner

*Primary Examiner*—Deepak Rao
(74) *Attorney, Agent, or Firm*—Rosenberg, Klein & Lee

(57) ABSTRACT

A fluorene-based pyrimidine-containing conjugated oligomer applied in six different layers in an OLED, respectively, used as an electron-transport emitting layer, an emitting layer, a host in the emitting layer, the ETL, a host in the electron-transport emitting layer, and a hole-blocking layer to upgrade light-emitting efficiency and regulate emitting color of the OLED.

12 Claims, 19 Drawing Sheets

F-1

F-2

2,7-bis[2-(4-tert-butylphenyl)pyrimidine-5-yl]-9,9'-spirobifluuorene

F-3

F-4

Device: ITO/PEDT:PSS (30 nm)/á-NPD (30 nm)/CBP (15 nm)/F-2 (30 nm)/Alq₃ (20 nm)/LiF (0.5 nm)/Al (150 nm), (a)

(b)

EQE: ~ 2.3%

Device 1 : ITO/PEDT:PSS(30 nm)/á-NPD (45 nm)/F-2:Perylene (1 wt.%, 30 nm)/Alq₃(20 nm)/LiF(0.5 nm)/Al(150 nm),
Device 2 : ITO/PEDT:PSS(30 nm)/á-NPD (25 nm)/NCB(20 nm)/F-2:Perylene (1 wt.%, 30 nm)/Alq₃(20 nm)/LiF(0.5 nm)/Al(150 nm),
Device 3 : ITO/PEDT:PSS(30 nm)/NCB (45 nm)/F-2:Perylene (1 wt.%, 30 nm)/Alq₃(20 nm)/LiF(0.5 nm)/Al(150 nm), Device 1 : ITO/PEDT:PSS(30 nm)/á-NPD (45 nm)/F-2:Perylene (1 wt.%, 30 nm)/Alq₃(20 nm)/LiF(0.5 nm)/Al(150 nm), Device 2 : ITO/PEDT:PSS(30 nm)/á-NPD (25 nm)/NCB(20 nm)/F-2:Perylene (1 wt.%, 30 nm)/Alq₃(20 nm)/LiF(0.5 nm)/Al(150 nm), Device 3 : ITO/PEDT:PSS(30 nm)/NCB (45 nm)/F-2:Perylene (1 wt.%, 30 nm)/Alq₃(20 nm)/LiF(0.5 nm)/Al(150 nm), EQE:
Device 1: ~ 3% ; Device 2: ~ 4% ; Device 3: ~ 4%

Device 1: ITO/PEDT:PSS (30 nm)/á-NPD (45 nm)/F-2:Perylene (1 wt.%, 25 nm)/F-2 (25 nm)/LiF (0.5 nm)/Al (150 nm),
Device 2: ITO/PEDT:PSS (30 nm)/á-NPD (45 nm)/F-2:Perylene (5 wt.%, 25 nm)/F-2 (25 nm)/LiF (0.5 nm)/Al (150 nm), (a)

Device 1: ITO/PEDT:PSS (30 nm)/á-NPD (45 nm)/F-2:Perylene (1 wt.%, 25 nm)/F-2 (25 nm)/LiF (0.5 nm)/Al (150 nm), Device 2: ITO/PEDT:PSS (30 nm)/á-NPD (45 nm)/F-2:Perylene (5 wt.%, 25 nm)/F-2 (25 nm)/LiF (0.5 nm)/Al (150 nm), EQE:
    Device 1: ~ 2.8% ; Device 2: ~ 3.2 %.

Device : ITO/PEDT:PSS (30 nm)/NCB (45 nm)/F-2:Perylene (1 wt.%, 50 nm)/LiF (0.5 nm)/Al (150 nm)

Device: ITO/PEDT:PSS (30 nm)/NCB (45 nm)/F-2:Perylene (1 wt.%, 50 nm)/LiF (0.5 nm)/Al (150 nm)

(b)

EQE: ~ 2.8%.

Device 1: ITO/PEDT:PSS (30 nm)/á-NPD (25 nm)/NCB (20 nm)/F-2 (30 nm)/Alq$_3$ (20 nm)/LiF (0.5 nm)/Al (150 nm),
Device 2: ITO/PEDT:PSS (30 nm)/NCB (45 nm)/F-2 (30 nm)/Alq$_3$ (20 nm)/LiF (0.5 nm)/Al (150 nm), (a)

Device 1: ITO/PEDT:PSS (30 nm)/á-NPD (25 nm)/NCB (20 nm)/F-2 (30 nm)/Alq$_3$ (20 nm)/LiF (0.5 nm)/Al (150 nm),

Device 2: ITO/PEDT:PSS (30 nm)/NCB (45 nm)/F-2 (30 nm)/Alq$_3$ (20 nm)/LiF (0.5 nm)/Al (150 nm), EQE:
    Device 1: ~ 2% ; Device 2: ~ 2%.

PYRIMIDINE SPIROBIFLUORENE OLIGOMER FOR ORGANIC LIGHT-EMITTING DEVICE

BACKGROUND OF THE INVENTION

1. Field of the Invention

The present invention is related to a fluorene-based pyrimidine-containing conjugated oligomer for organic light-emitting device.

2. Description of the Prior Art

In the known technical field of organic light-emitting materials when a small molecule compound is used as the organic light-emitting material, crystallization usually occurs due to the molecular of the compound is too small and its structure is too symmetrical. Therefore, when applied as an organic light-emitting material, the small molecule compound is vulnerable to crystallization, and once the crystal is formed, it yields negative impacts upon the light-emitting nature and service life of the OLED. Such flaws caused by the restriction from the compound structure cannot be easily overcome and eliminated.

Furthermore, those valance electrons involving in the bonding process is another existing problem to the organic light-emitting device since the they when excited to become free electrons, they form a hole and the hole has a greater moving rate and that of the electrons, resulting in reduced chance for further bonding or if bonded, that takes place in a layer of the device not pre-determined. In terms of a structure of an organic light-emitting device (1) as illustrated in FIG. 1 of the accompanying drawings, an electron-transport layer and a hole transport layer (3) are respectively connected to an electric field (6) through a metal cathode (4) and an indium tin oxide (ITO) anode (5), given with the externally applied electric filed, electrons from the electron transport layer (2) and the hole from the hole transport layer (3) both enter into an organic light-emitting layer (7) to further bond into excitons to release the energy and return to the ground level. In the course of releasing the energy, it is representing by lights of various colors depending on the material used for the organic light-emitting layer (7). Before the moving rate of the electron become optimal, if the reaction of the further bonding fails to present in the organic light-emitting layer (7), the electroluminescent efficiency is naturally compromised and deprived of the value of the OLED for industrial purpose.

SUMMARY OF THE INVENTION

The primary purpose of the present invention is to provide a fluorene-based pyrimidine-containing conjugated oligomer for an organic light-emitting device with its molecular structure capable of blocking the interaction among molecules thus to prevent the crystallization by the molecules.

Another purpose of the present invention is to provide a fluorene-based pyrimidine-containing conjugated oligomer for an organic light-emitting device given with the nature of electron transport to overcome the problem of comparatively lower moving rate of the electrons by the prior art.

To achieve the purposes, the compound formula of the present invention is stated as follows:

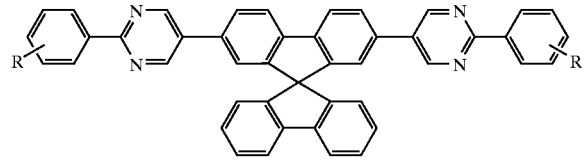

Wherein, R represents —$OC_nH_{2n+1}$ (n=1~4), —$C_4H_9$, —$C_8H_5$ or H.

DETAILED DESCRIPTION OF THE INVENTION

In the description of its application in an OLED, a compound of the present invention has its compound structure as disclosed below:

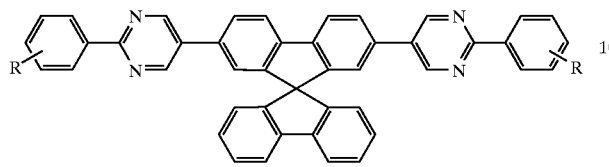

Wherein, the replacement group located at where bonded to the peripheral of a pyrimidine relates to a group of 4-n-butyoxy (4-OC$_4$H$_9$) (F1), 4-tertiary-butyl (F2), 4-methoxyl (4-OCH$_3$)(F3), or 3-methoxyl (3-OCH$_3$)(F4).

Two feasible processes are available for the present invention. Firstly, boric acid initiators 2, 3, 4, and 5 needed in the Suzuki coupling reaction are used to respectively undergo coupling reaction with a 2-brome-5-iodo-pyrimidine using a Pd (PPh$_3$)$_4$ as catalyst to produce Compound 6 (yield: 70%), Compound 7 (yield: 82%), Compound 8 (yield: 79%), and Compound 9 (yield: 83%) as stated below (Formula 16):

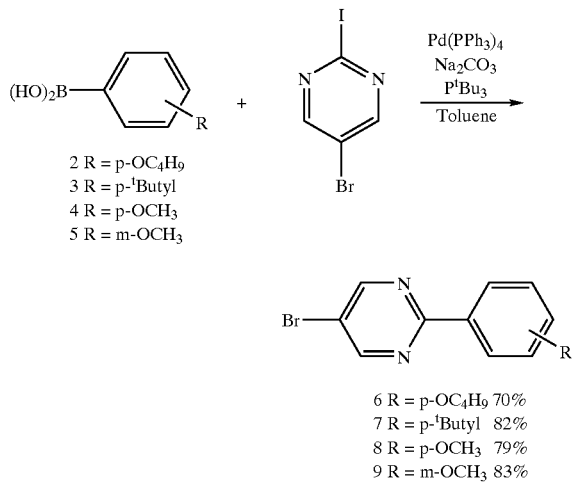

Those resultant synthetic pyrimidine unit compounds 6, 7, 8, and 9 as well as spirobifluorene compound 21 containing diboric acid ester are undergoing once again the Suzuki coupling reaction to avail respectively final products of F1~F4 each with the nitrogen replacement location on the cyclic side chain of pyrimidine facing outward as illustrated below:

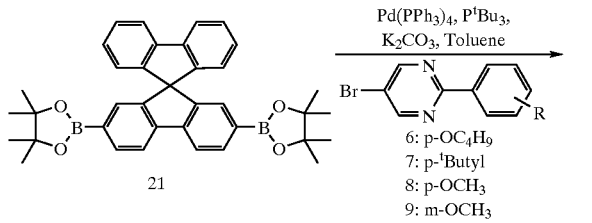

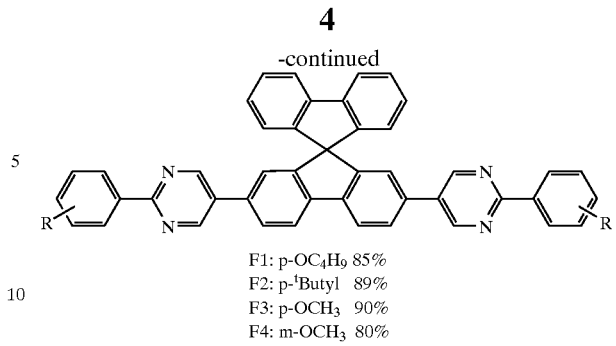

F1: p-OC$_4$H$_9$ 85%
F2: p-$^t$Butyl 89%
F3: p-OCH$_3$ 90%
F4: m-OCH$_3$ 80%

Secondly, in the synthesis of oligomer at where facing inwardly on the pyrimidine cyclic chain, the Suzuki coupling reaction is used for the spirobifluorene compound 21 containing diboric acid ester and 2-brome-5-iodo pyrimidine with Pd(PPh3)4 as the catalyst to avail a compound (yield: 85%) with the nitrogen replacement location on the cyclic side chain of pyrimidine facing inward as illustrated below:

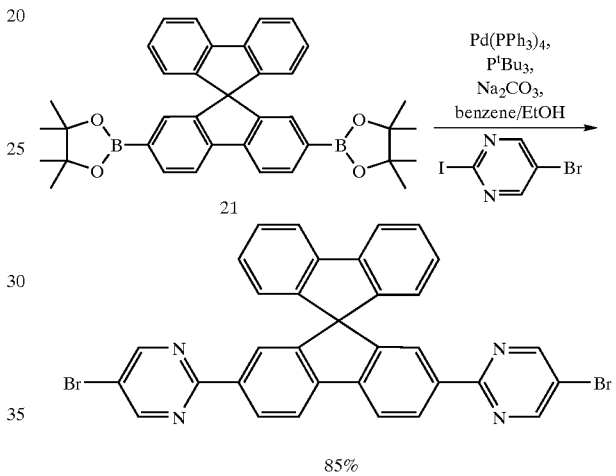

After the selected synthesis to avail the intermediate compound containing pyrimidine unit with nitrogen facing the spirobifluorene group, the Suzuki coupling reaction is used once again to have boric acid reagent either of the same or the different replacement group on the benzene cyclic chain but with a different replacement location to undergo the coupling reaction. Consequently, a target oligomer having two nitrogen atoms of the pyrimidine cycle on the backbone to face the spirodiafluorene is produced.

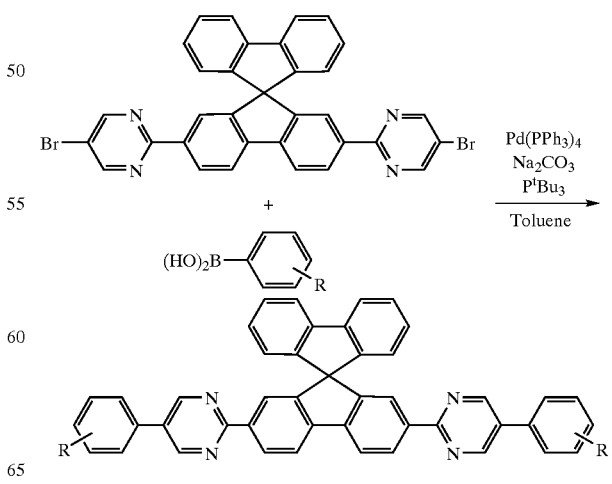

Figure 2:
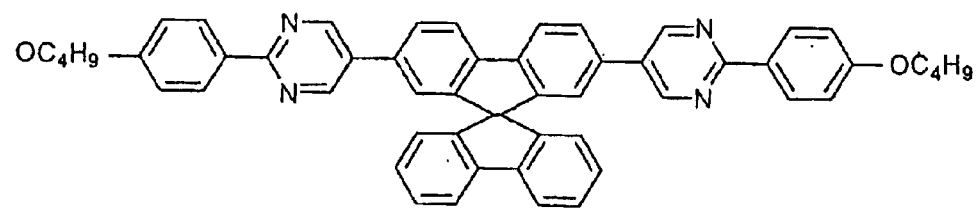
FIG. 2 is a view of an absorption spectrum of UV-visible light with a 4-n-butyoxy group (F1) as a replacement group in bonding the fluorene-based pyrimidine-containing conjugated oligomer to the cyclic side chain of pyrimidine.
Figure 2:
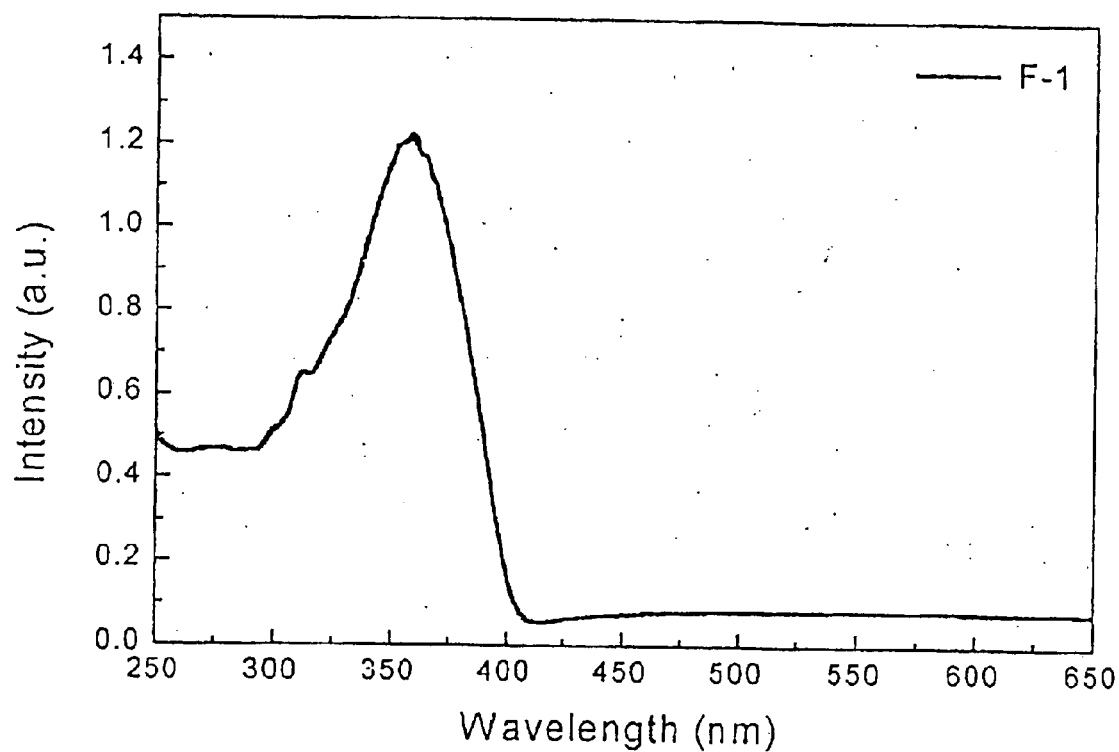

Based on the spectra available from experiments separately conducted, the optical and physical characteristics in the production of the present invention into a solid-status film are described. Wherein, as illustrated in FIG. 2 shows an absorption spectrum of UV-visible light with a 4-n-butyoxy group (F1) as a replacement group in bonding the fluorene-based pyrimidine-containing conjugated oligomer to the cyclic side chain of pyrimidine.

Figure 3:
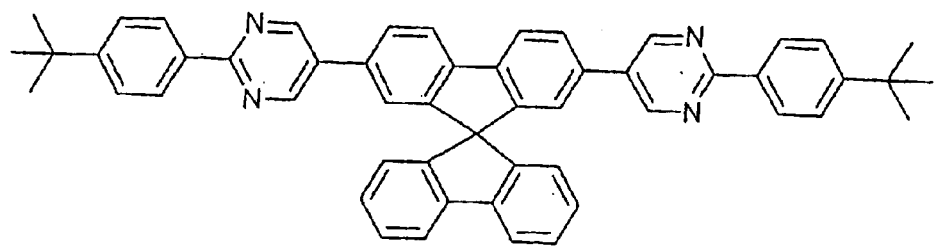
FIG. 3 is a view of an absorption spectrum of the UV-visible light with a 4-tertiary butyl group (F2) as a replacement group in bonding the fluorene-based pyrimidine-containing conjugated oligomer to the cyclic side chain of pyrimidine.
Figure 3:
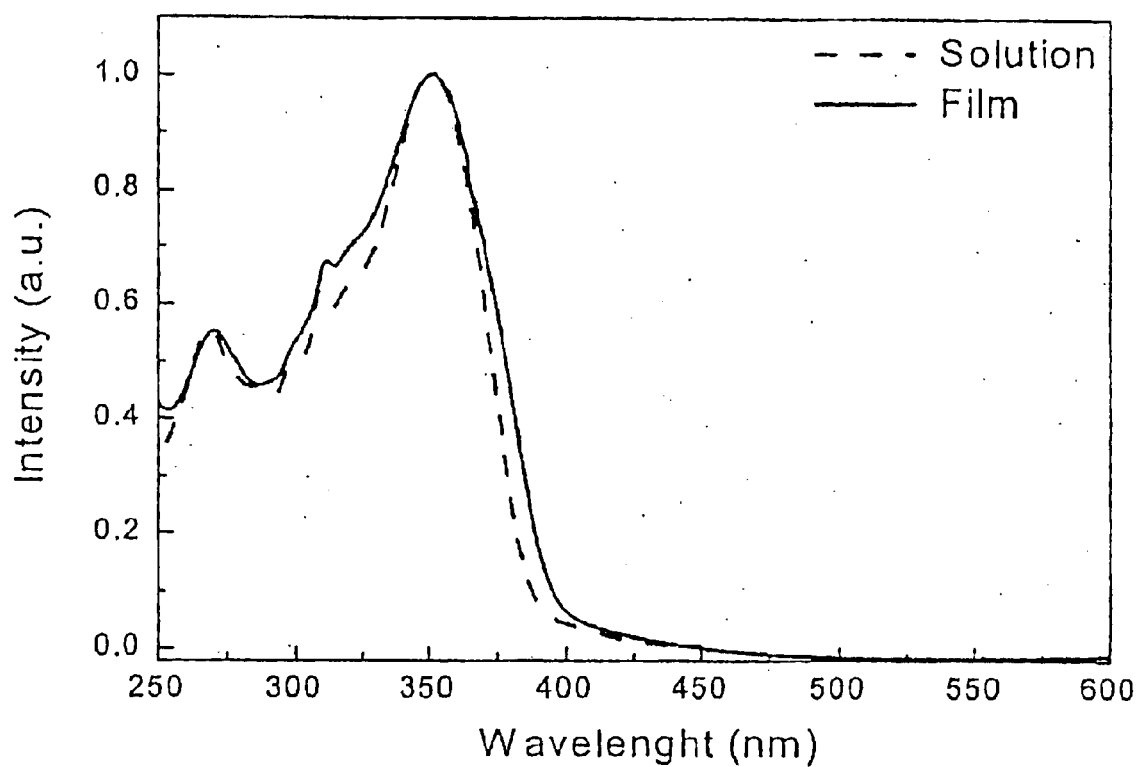

FIG. 3 shows an absorption spectrum of the UV-visible light with a 4-tertiary butyl group (F2) as a replacement group in bonding the fluorene-based pyrimidine-containing conjugated oligomer to the cyclic side chain of pyrimidine.

Figure 4:
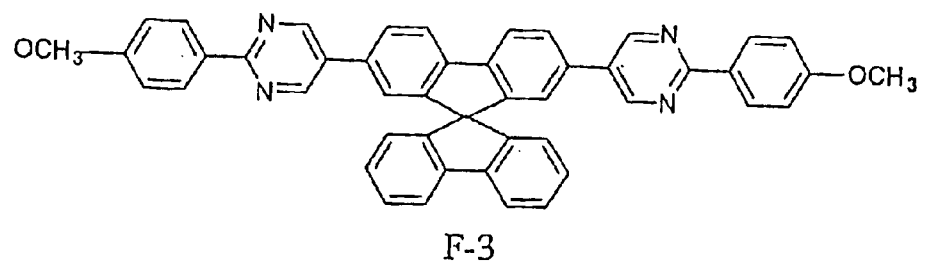
FIG. 4 is a view of an absorption spectrum of the UV-visible light with a 4-methoxyll group (F3) as a replacement group in bonding the fluorene-based pyrimidine-containing conjugated oligomer to the cyclic side chain of pyrimidine.
Figure 4:
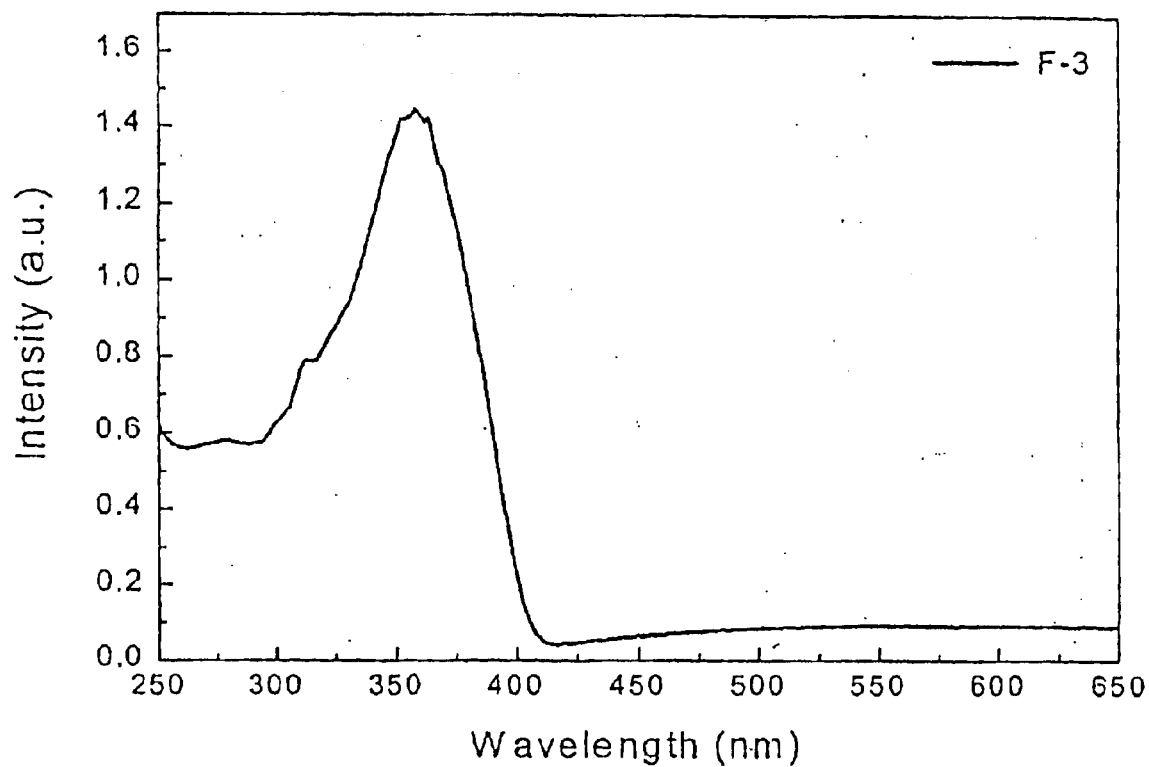

FIG. 4 shows an absorption spectrum of the UV-visible light with a 4-methoxyl group (F3) as a replacement group in bonding the fluorene-based pyrimidine-containing conjugated oligomer to the cyclic side chain of pyrimidine.

Figure 5:
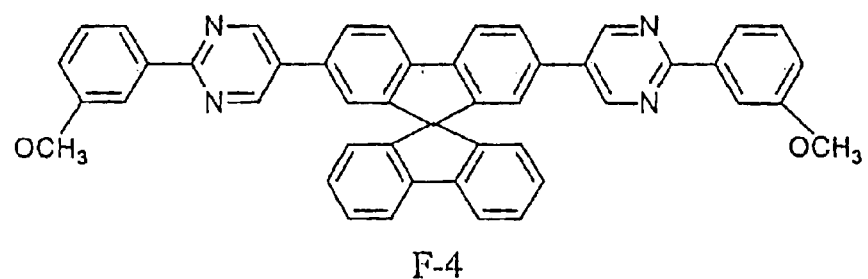
FIG. 5 is a view of an absorption spectrum of the UV-visible light with a 3-methoxyll group (F4) as a replacement group in bonding the fluorene-based pyrimidine-containing conjugated oligomer to the cyclic side chain of pyrimidine.
Figure 5:
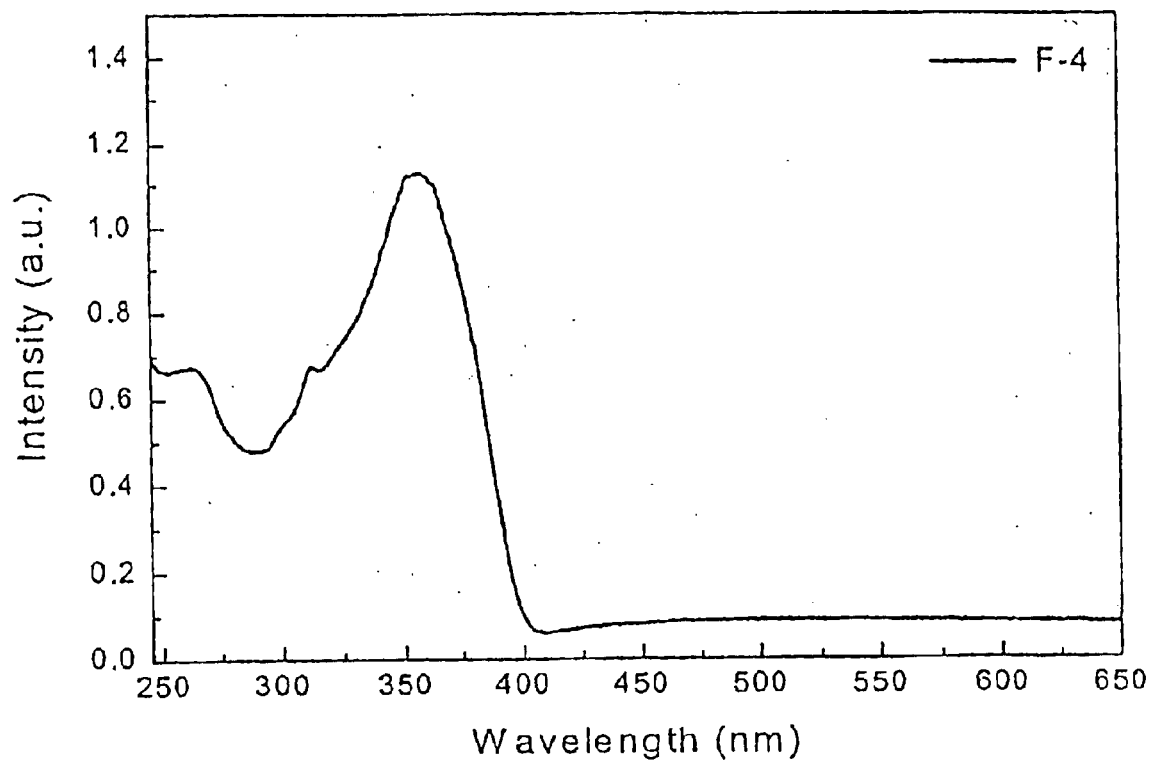

FIG. 5 shows an absorption spectrum of the UV-visible light with a 3-methoxyl group (F4) as a replacement group in bonding the fluorene-based pyrimidine-containing conjugated oligomer to the cyclic side chain of pyrimidine.

Figure 6:
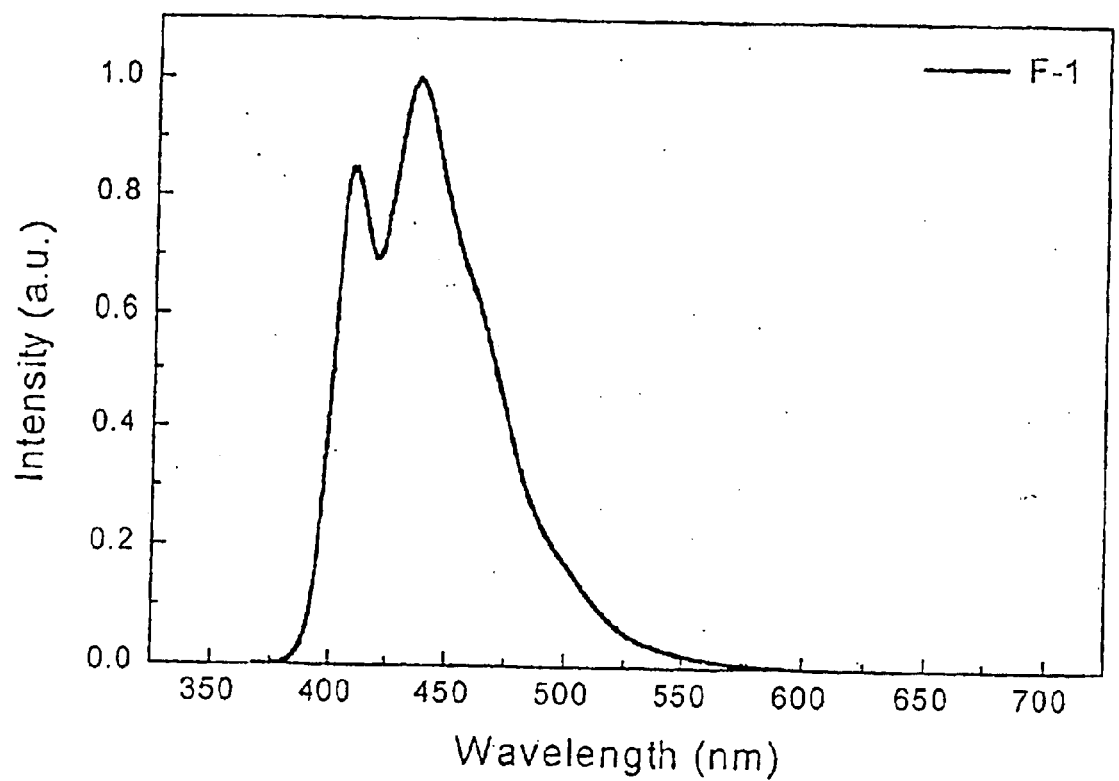
FIG. 6 is a view of a photoluminescence spectrum of fluorescence radiation with a 4-n-butyoxy group (F1) as a replacement group in the bonding of the fluorene-based pyrimidine-containing conjugated oligomer to the cyclic side chain of pyrimidine.

FIG. 6 shows a photoluminescence spectrum of fluorescence radiation with a 4-n-butyoxy group (F1) as a replacement group in the bonding of the fluorene-based pyrimidine-containing conjugated oligomer to the cyclic side chain of pyrimidine.

Figure 7:
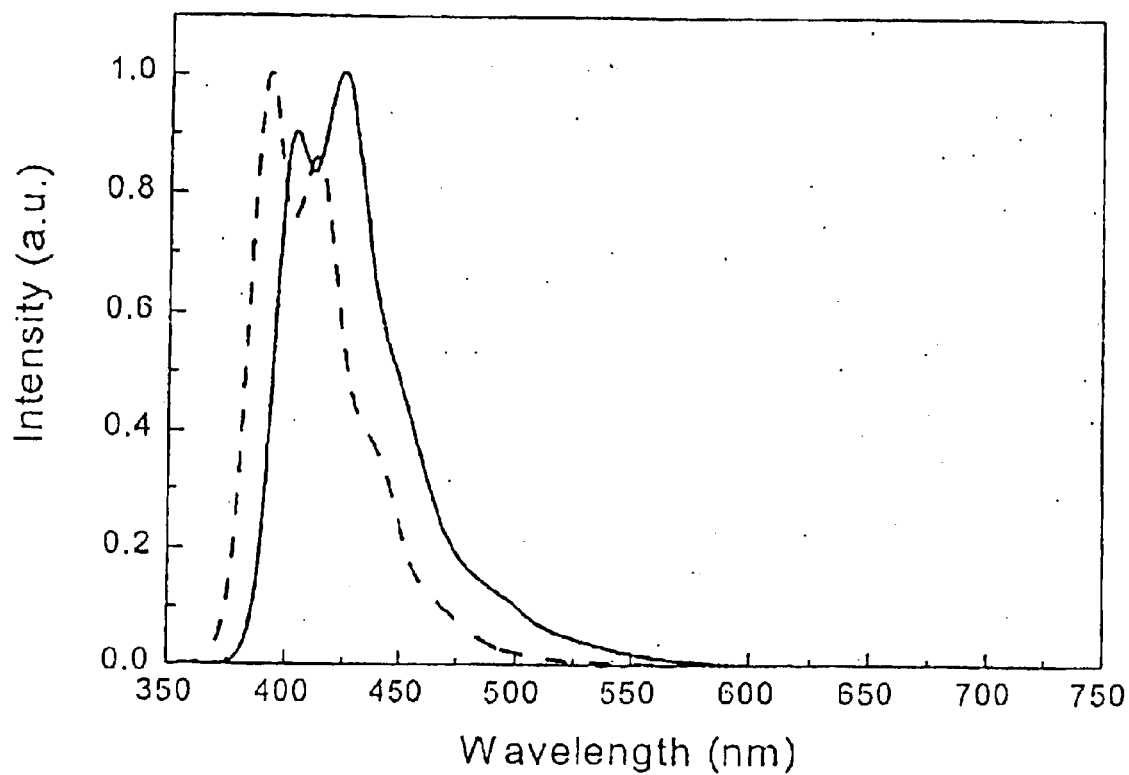
FIG. 7 is a view of a photoluminescence spectrum of fluorescence radiation with a 4-tertiary butyl group (F2) as a replacement group in the bonding of the fluorene-based pyrimidine-containing conjugated oligomer to the cyclic side chain of pyrimidine.

FIG. 7 shows a photoluminescence spectrum of fluorescence radiation with a 4-tertiary butyl group (F2) as a replacement group in the bonding of the fluorene-based pyrimidine-containing conjugated oligomer to the cyclic side chain of pyrimidine.

Figure 8:
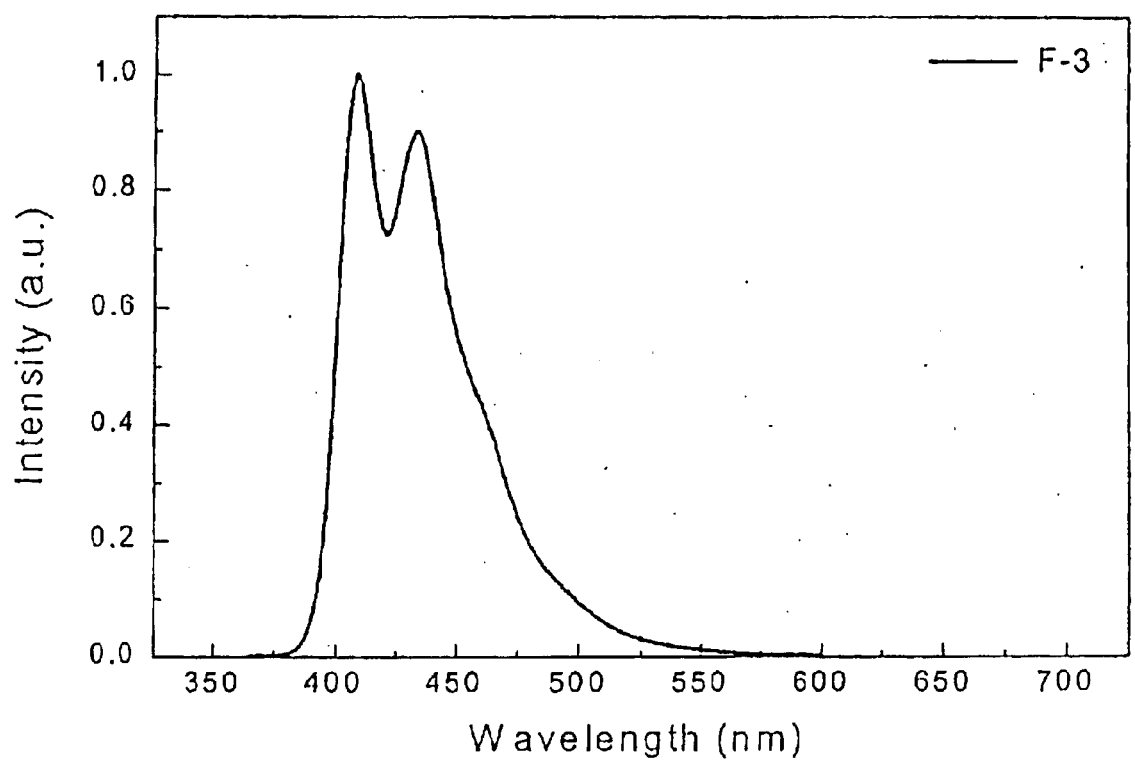
FIG. 8 is a view of a photoluminescence spectrum of fluorescence radiation with a 4-methoxyl group (F3) as a replacement group in the bonding of the fluorene-based pyrimidine-containing conjugated oligomer to the cyclic side chain of pyrimidine.

FIG. 8 shows a photoluminescence spectrum of fluorescence radiation with a 4-methoxyl group (F3) as a replacement group in the bonding of the fluorene-based pyrimidine-containing conjugated oligomer to the cyclic side chain of pyrimidine.

Figure 9:
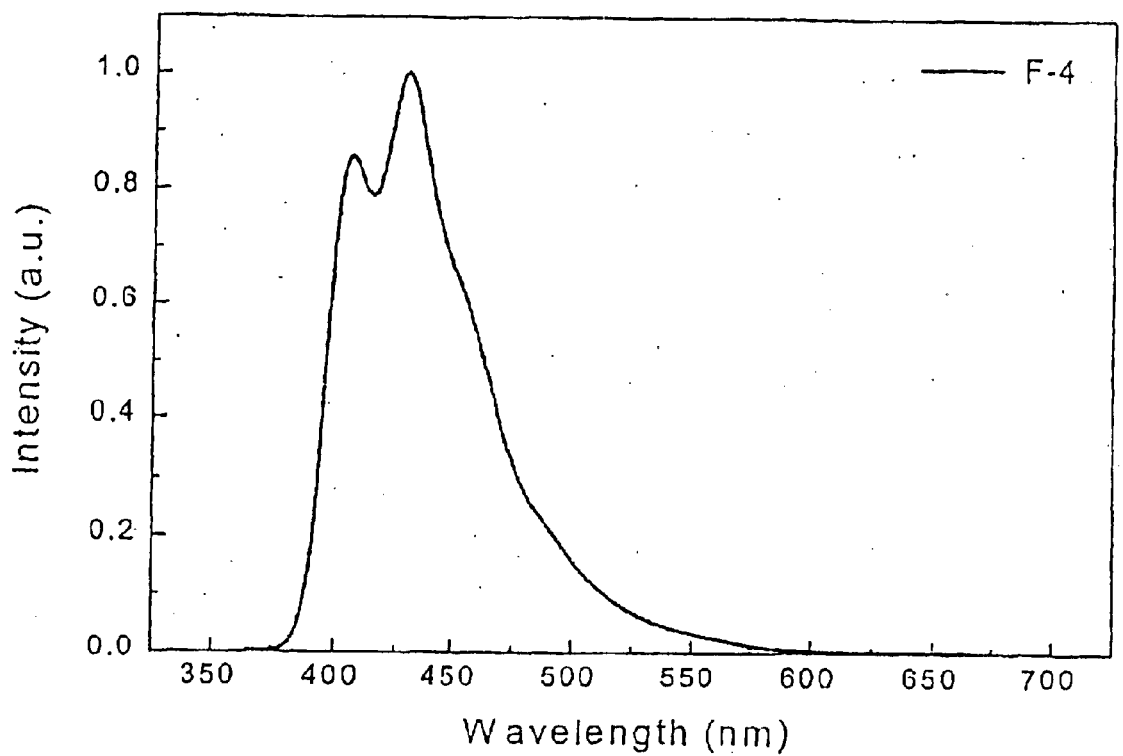
FIG. 9 is a view of a photoluminescence spectrum of fluorescence radiation with a 3-methoxyl group (F4) as a replacement group in the bonding of the fluorene-based pyrimidine-containing conjugated oligomer to the cyclic side chain of pyrimidine.

FIG. 9 shows a photoluminescence spectrum of fluorescence radiation with a 3-methoxyl group (F4) as a replacement group in the bonding of the fluorene-based pyrimidine-containing conjugated oligomer to the cyclic side chain of pyrimidine.

For a general compound made into a solid status film, its UV-visible absorption spectrum will demonstrate a wider absorption peak accompanied with a phenomenon known as red shift compared to that taken in solution status. The reason is that under the solid status film, the profile of molecules has a wider distribution while the spacing among molecules is shortened often resulting in ô- ô interaction created on the coordinate bond, further to cause wider distribution of the energy levels of HOMO and LUMO, and narrower gap between energy levels, and finally, the wider absorption peak and the phenomenon of red shift.

Referring to FIGS. 2 through 5, though the wider peak is observed, there is negligible red shift to its $\ddot{e}_{max}$ and nor any significant ô- ô interaction created. That is, comparatively diversified molecule profile contributes to the wider absorption peak. In other words, each oligomer of the present invention provides the 3D results of fully blocking the spirobifluorene, and no significant red shift is observed in any of the absorption spectra of the present invention when made into a solid status film.

As exhibited in the photoluminescence spectra illustrated in FIGS. 6 through 9, all the oligomers provided by the present invention when each made into a solid status film are observed with the following characteristics compared to when they are in solution status.

Firstly, approximately only 10~15 nm of $\ddot{e}_{max}$ red shift is observed to provide excellent consistence when compared to the prior art since the red shift is a common phenomenon observed in the film made from oligomer in solution status.

Secondary, even with the wider $W_{1/2}$, all stay well below 70 nm; it is considered as a material with narrow wave region and pure chrominance that to any organic light-emitting device.

Figure 1:
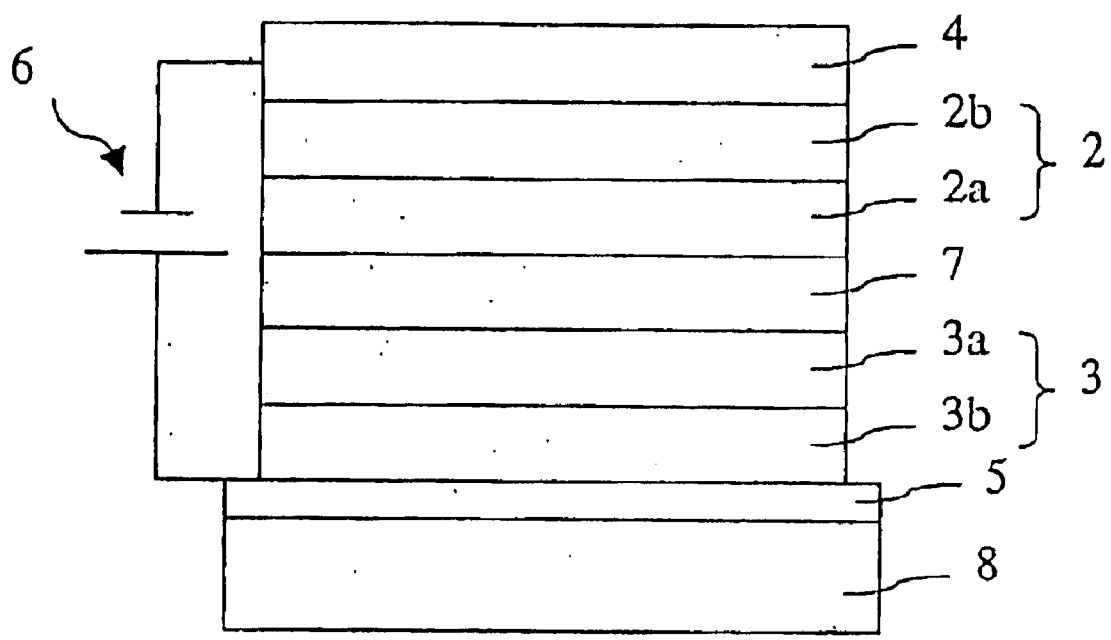
FIG. 1 is a schematic view showing the structure of multiple layers of an organic light-emitting device.

When applied in an OLED, the fluorene-based pyrimidine-containing conjugated oligomer of the present invention occupies a proper layer in the structure of the OLED as illustrated in FIG. 1. Wherein, the electron layer (2) of the OLED (1) contains an electron transport layer (2a) and an electron injection layer (2b) while a hole layer (3) contains a hole transport layer (3a) and a hole injection layer (3b). Both of the EIL (2b) and the HIL (3b) are provided to improve conductivity between a cathode (4) and the ETL (2a) as well as between an ITO anode (5) and the HTL (3a) thus to reinforce the injection of the electron and the hole.

The fluorene-based pyrimidine-containing conjugated oligomer of the present invention is further applied in six different layers in an OLED, respectively, an electron-transport emitting layer, an emitting layer, a host in the emitting layer, the ETL, a host in the electron-transport emitting layer, and a hole blocking layer with their preferred embodiments to be each described as follows:

In the first preferred embodiment where the present invention is applied as an electron-transport emitting layer in OLEDs, the film of each of those fluorene-based pyrimidine-containing conjugated oligomer of the present invention is applied in a multiplayer OLED adapted with other materials as the electron-transport emitting layer in the production of the following OLED due to that it provides higher negative charge (electron) affinity and higher electroluminescent efficiency: glass substrate/ITO/PEDT: PSS (30 nm)/á-NPD (30 nm)/CBP (15 nm)/Pyrimidine compound F-2 (50 nm)/LiF (0.5 nm)/Al (150 nm).

Figure 10:
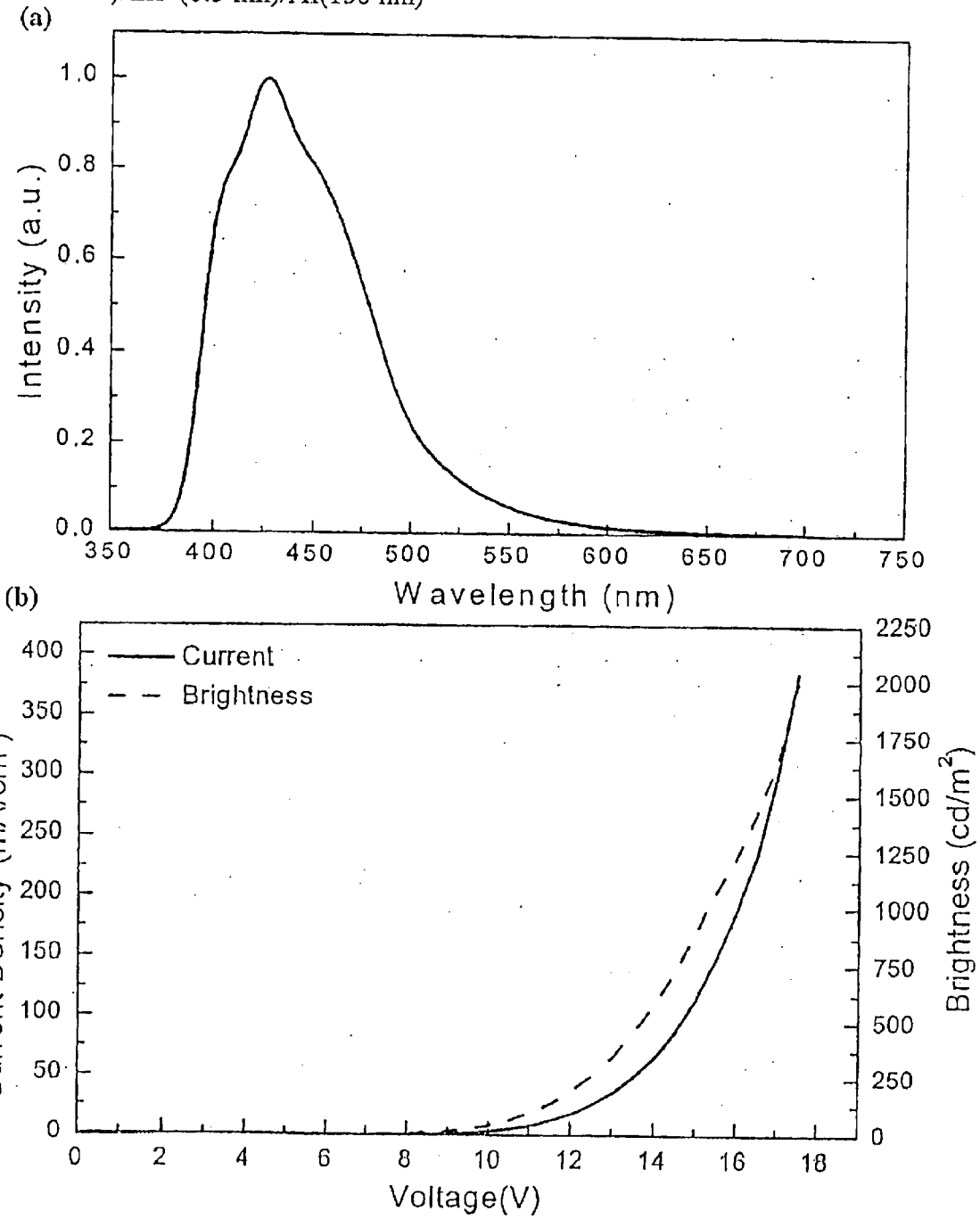
FIG. 10 is a view of light-emitting characteristic with a Current-Voltage-Brightness curve of an OLED of a first preferred embodiment of the present invention.

FIG. 10 shows a light-emitting characteristic with a Current-Voltage-Brightness curve of an OLED of the first preferred embodiment of the present invention.

As illustrated, the photoluminescence characteristic of the OLED shows the blue light emission for containing fluorene-based pyrimidine-containing conjugated oligomer and it is confirmed that the fluorene-based pyrimidine-containing conjugated oligomer does provide the functions as the electron transport layer also as an emitting layer in OLEDs. When so used, the fluorene-based pyrimidine-containing conjugated oligomer provides comparatively high current density for the OLED and to cause the OLED producing comparatively higher brightness (>2000 cd/m$^2$) to give the ~2.3% maximal external electroluminescence quantum efficiency.

Whereas the OLED has the fluorene-based pyrimidine-containing conjugated oligomer free of dopants as the emitting layer, anyone who is familiar with the art of OLED knows that the electroluminescent efficiency and the regulation of the emitting color can be upgraded for the OLED when a highly efficient emission dopant is provided; and knows that the fluorene-based pyrimidine-containing conjugated oligomer can be applied in various structures of devices to function as the electron-transport emitting layer or a part of the layer.

In a secondary preferred embodiment of the present invention, fluorene-based pyrimidine-containing conjugated oligomer of the present invention is applied as the emitting layer in OLEDs. Whereas the film of the fluorene-based pyrimidine-containing conjugated oligomer provides at the same time good thermal stability and high photoluminescence quantum yield, it is applied in the multiplayer OLED adapted with other materials as the emitting layer for the production of the OLED described as having glass substrate/ ITO/PEDT: PSS (30 nm)/á-NPD (30 nm)/CBP (15 nm)/ Pyrimidine compound F-2 (30 nm)/Alq$_3$ (20 nm)/LiF (0.5 nm)/Al (150 nm).

Figure 11:
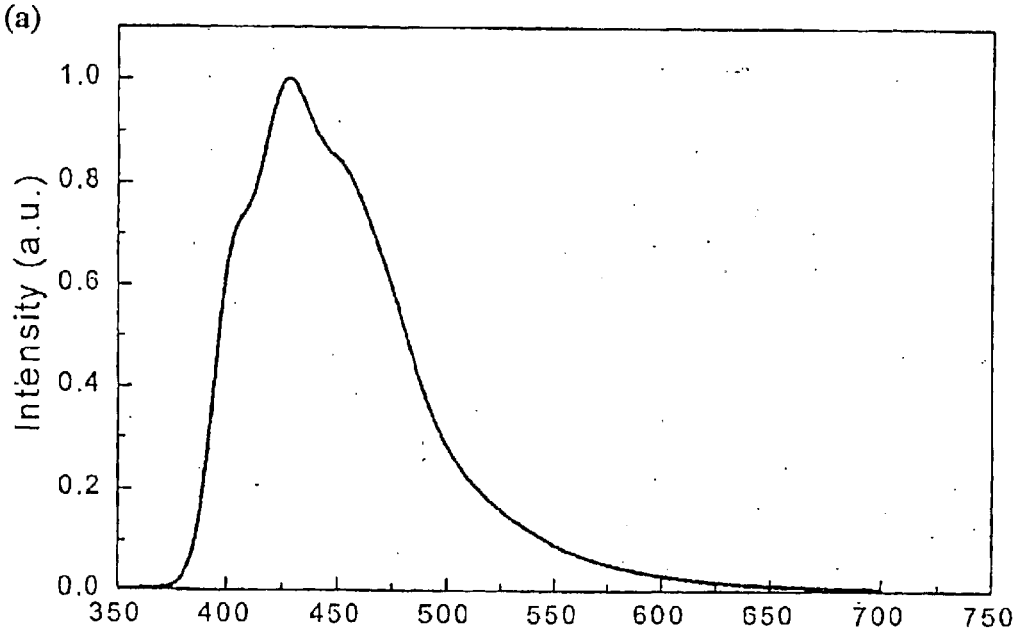
FIG. 11 is a view of light-emitting characteristic with a Current-Voltage-Brightness curve of an OLED of a second preferred embodiment of the present invention.
Figure 11:
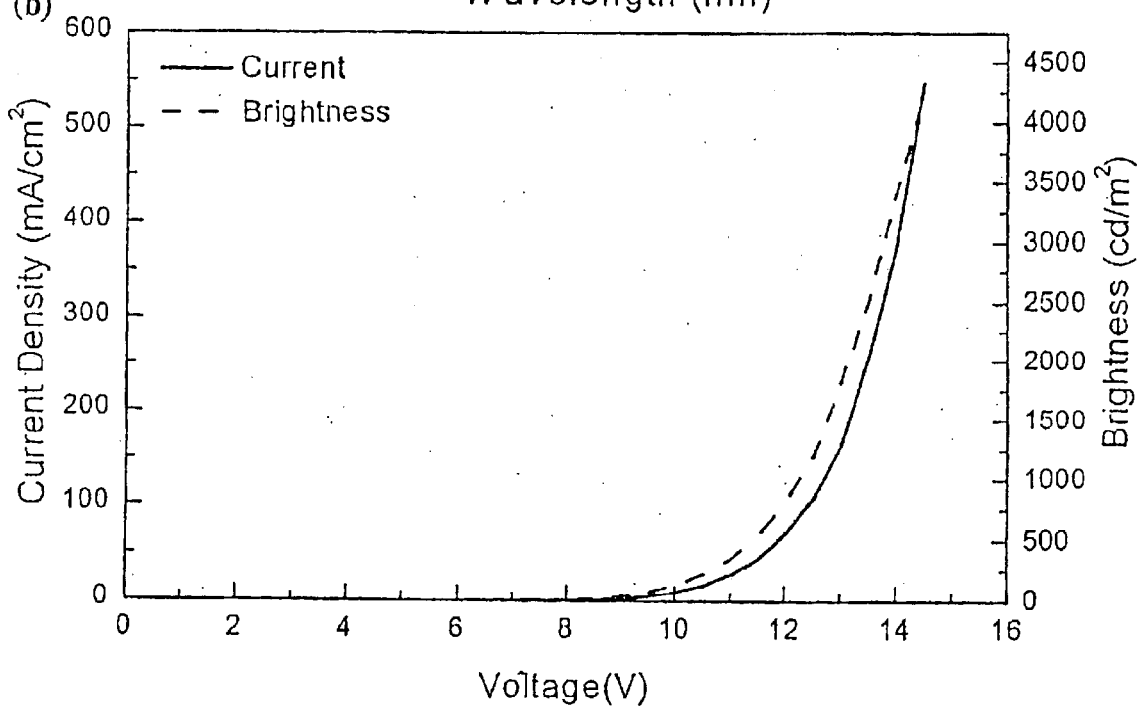

FIG. 11 shows a light-emitting characteristic with a Current-Voltage-Brightness curve of an OLED of the second preferred embodiment of the present invention.

As illustrated, the light emitting characteristic of the OLED exhibits the blue light emission of the fluorene-based pyrimidine-containing conjugated oligomer thus to confirm that the fluorene-based pyrimidine-containing conjugated oligomer does provide the function as an emitting layer in the OLED.

The use of fluorene-based pyrimidine-containing conjugated oligomer as the emitting layer attributes to the OLED to produce comparatively higher brightness (>4300 cd/m$^2$) and give the ~2.3% maximal external electroluminescent quantum efficiency.

It is to be noted that anyone who is familiar with the art of OLED knows that whereas the OLED has the fluorene-based pyrimidine-containing conjugated oligomer free of dopants as the emitting layer, the electroluminescent efficiency and the regulation of the emitting color can be upgraded for the OLED when a highly efficient emission dopant is provided; and knows that the fluorene-based pyrimidine-containing conjugated oligomer can be applied in various structures of devices to function as the emitting layer or a part of the layer.

In a third preferred embodiment of the present invention, the fluorene-based pyrimidine-containing conjugated oligomer of the present invention is used as a host in the emitting layer of OLEDs. Since each of the fluorene-based pyrimidine-containing conjugated oligomer films provides good thermal stability and proper distribution of energy levels, it is applied in multiplayer OLED adapted with doping technology to function as the host of the emitting layer for the production of the following three types of OLEDs:

Device 1: glass substrate/ITO/PEDT: PSS (30 nm)/á-NPD (45 nm)/CBP (15 nm)/Pyrimidine compound F-2: Perylene (1 wt. %, 30 nm)/Alq$_3$ (20 nm)/LiF (0.5 nm)/Al (150 nm);

Device 2: glass substrate/ITO/PEDT: PSS (30 nm)/α-NPD (25 nm)/NCB (20 nm)/Pyrimidiine compound F-2: Perylene (1 wt. %, 30 nm)/Alq$_3$ (20 nm)/LiF (0.5 nm)/Al (150 nm); and Device 3: glass substrate/ITO/PEDT: PSS (30 nm)/NCB (45 nm)/Pyrimidine compound F-2: Perylene (1 wt. %, 30 nm)/Alq$_3$ (20 nm)/LiF (0.5 nm)/Al (150 nm).

Figure 12A:
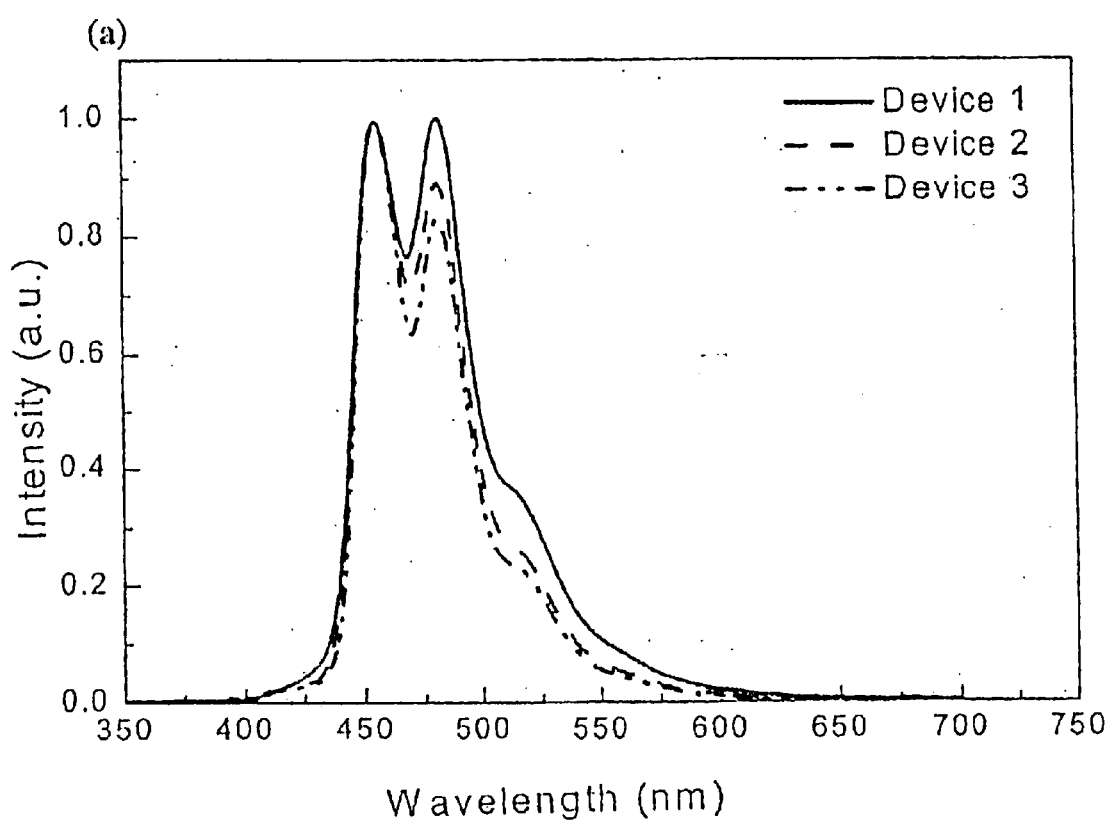
FIGS. 12a and b show a view of light-emitting characteristic with a Current-Voltage-Brightness curve of an OLED of a third preferred embodiment of the present invention.
Figure 12B:
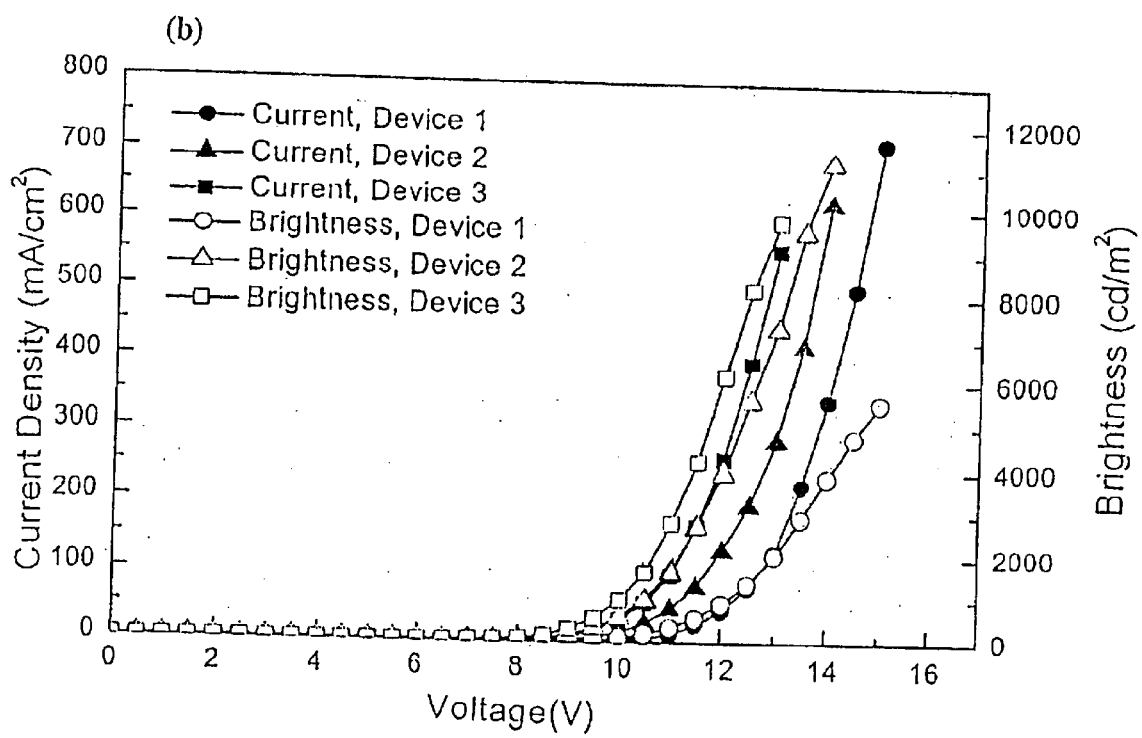

FIG. 12a and 12b show a light-emitting characteristic with a Current-Voltage-Brightness curve of an OLED of the third preferred embodiment of the present invention.

The light-emitting characteristic exhibited shows the blue light emission of the fluorene-based pyrimidine-containing conjugated oligomer of the present invention to confirm that the fluorene-based pyrimidine-containing conjugated oligomer gives excellent energy transfer mechanism in the OLEDs to promote the organic fluorescence dyestuff of Perylene to emit light.

As also illustrated in the curve, when the α-NPD or NCB is used as the HTL, either is capable of providing the OLED comparatively high current density and brightness (>5000 cd/m$^2$ in case of Device 1;>10000 cd/m$^2$, Device 2; and >9000 cd/m$^2$, Device 3).

Meanwhile, all three Devices give the ~3.0–4.0% maximal external electroluminescence quantum efficiency, quite high for any doping type of blue light-emitting device.

Whereas trace of guest emissive dopants such as perylene is doped to the fluorene-based pyrimidine-containing conjugated oligomer in any of those OLEDs as the emitting layer, anyone who is familiar with the art of OLED should know that the fluorene-based pyrimidine-containing conjugated oligomer is capable of being used as a host or a part of host in various structures of OLEDs.

In a fourth preferred embodiment of the present invention, the fluorene-based pyrimidine-containing conjugated oligomer is used as an ETL in OLEDs. Since each of the films made out of those fluorene-based pyrimidine-containing conjugated oligomer gives comparatively higher negative charge (electron) affinity and properly distributed energy levels, it is capable of being applied in a multiplayer OLED adapted with other materials as the ETL for the production of the following OLEDs:

Device 1: glass substrate/ITO/PEDT: PSS (30 nm)/α-NPD (45 nm)/Pyrimidine compound F-2: Perylene (1 wt. %, 25 nm)/F-2 (25 nm)/LiF (0.5 nm)/Al (150 nm); and Device 2: glass substrate/ITO/PEDT: PSS (30 nm)/α-NPD (45 nm)/Pyrimidine compound F-2: Perylene (5 wt. %, 25 nm)/F-2 (25 nm)/LiF (0.5 nm)/Al (150 nm).

Figure 13A:
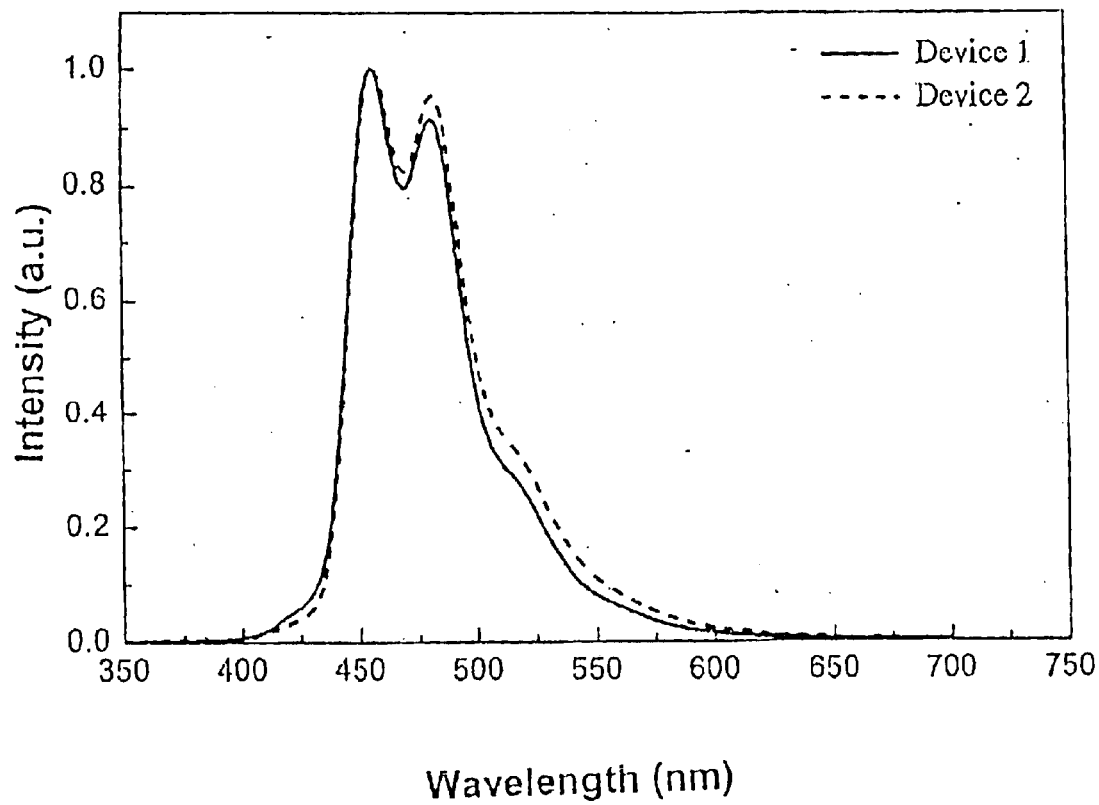
FIGS. 13a and 13b show a view of light-emitting characteristic with a Current-Voltage-Brightness curve of an OLED of a fourth preferred embodiment of the present invention.
Figure 13B:
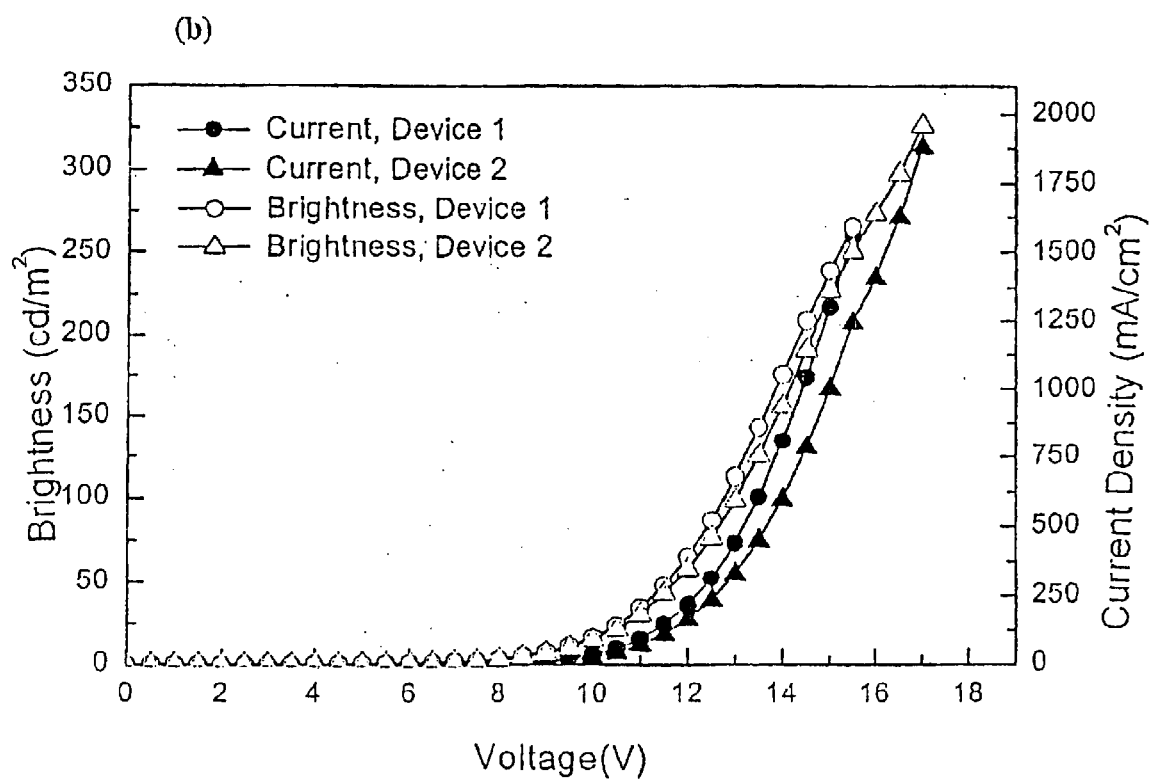

FIGS. 13a and 13b shows a light-emitting characteristic with a Current-Voltage-Brightness curve of an OLED of the fourth preferred embodiment of the present invention.

As illustrated, the light-emitting characteristic demonstrates the blue light emission and it can be confirmed that the fluorene-based pyrimidine-containing conjugated oligomer is capable of transmitting electrons to the light-emitting layer in an OLED.

When the fluorene-based pyrimidine-containing conjugated oligomer is used as the hosts of the electron transport layer and the light-emitting layer adapted with Perylene as the guest emissive dopant to provide comparatively high current density and brightness (~1600–2000 cd/m2) for the OLED while both of Devices 1 and 2 give ~2.8%–3.2% maximal external electroluminescent quantum efficiency.

In this preferred enmbodimnent, trace of guest emissive dopant, Perylene is doped to the fluorene-based pyrimidine-containing conjugated oligomer to function as the light-emitting layer. Anyone who is familiar with the art of OLED should know that the fluorene-based pyrimidine-containing conjugated oligomer is capable of being properly applied in various structures of devices as the electron transport layer or a part of it.

In a fifth preferred embodiment of the present invention, the fluorene-based pyrimidine-containing conjugated oligomer is used as an electron-transport host layer in OLEDs. Since each of those films made from the fluorene-based pyrimidine-containing conjugated oligomer gives comparatively high negative charge (electron) affinity and properly distributed energy levels to be applied in the multiplayer OLED adapted with other materials as the electron-transport host layer for the production of the OLED described as having glass substrate/ITO/PEDT: PSS (30 nm)/NCB(45 nm)/Pyrimidine compound F-2: Perylene (1 wt. %, 50 nm)/LiF (0.5 nm)/Al (150 nm).

Figure 14A:
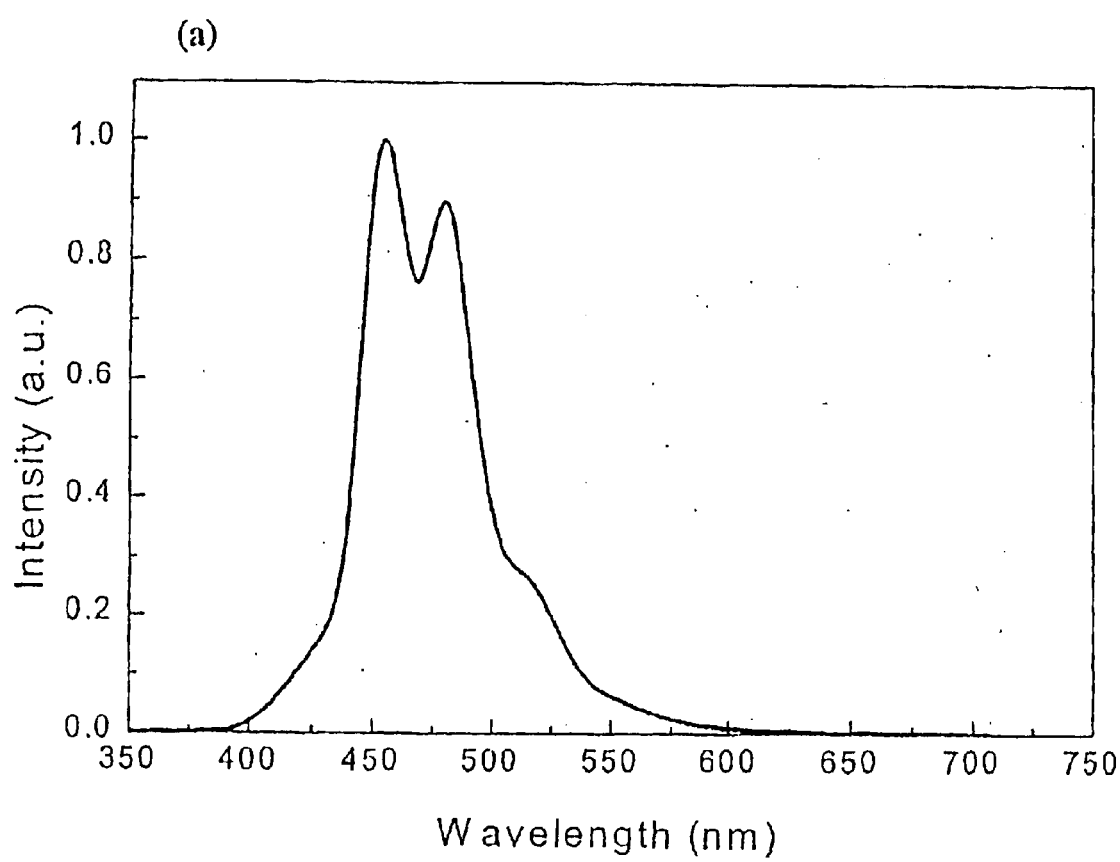
FIGS. 14a and 14b show a view of light-emitting characteristic with a Current-Voltage-Brightness curve of an OLED of a fifth preferred embodiment of the present invention.
Figure 14B:
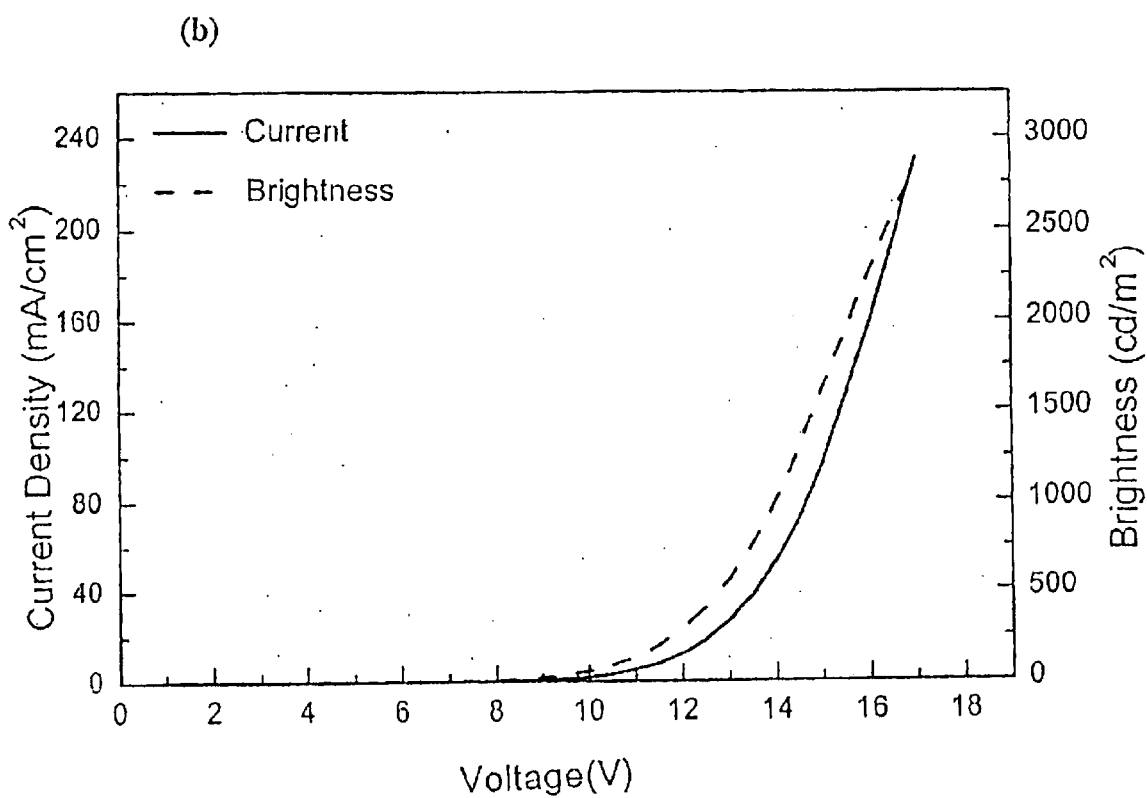

FIGS. 14a and 14b show a view of light-emitting characteristic with Current-Voltage-Brightness curve of an OLED of the fifth preferred embodiment of the present invention.

As illustrated, the light-emitting characteristic demonstrates the blue light emission and it can be confirmed that the fluorene-based pyrimidine-containing conjugated oligomer is capable of transmitting electrons to the light emitting layer and providing energy transfer in an OLED.

When used as the host of the electron transport layer, the fluorene-based pyrimidine-containing conjugated oligomer provides for the OLED comparatively high amperage and brightness (>2800 cd/m$^2$) to give the ~2.8% maximal external electroluminescent quantum efficiency).

In this preferred embodiment, trace of guest emissive dopant, Perylene, is doped to the fluorene-based pyrimidine-containing conjugated oligomer to function as the emitting layer. Anyone who is familiar with the art of OLED should know that the fluorene-based pyrimidine-containing conjugated oligomer is capable of being properly applied in various structures of devices as the host of the electron transport layer or a part of it.

In a sixth preferred embodiment of the present invention, the fluorene-based pyrimidine-containing conjugated oligomer is used as the hole-blocking layer in OLEDs. Since those films made from the fluorene-based pyrimidine-containing conjugated oligomer give comparatively high negative charge (electron) affinity and properly distributed of energy levels, they are capable of being applied in a multiplayer OLED adapted with other materials to function as the hole blocking layer for the production of the following two OLEDs:

Device 1: glass substrate/ITO/PEDT: PSS (30 nm)/α-NPC (25 nm)/NCB (20 nm)/Pyrimidine compound F-2 (30 nm)/Alq$_3$ (20 nm)/LiF (0.5 nm)/Al (150 nm); and Device 2: glass substrate/ITO/PEDT: PSS (30 nm)/NCB (45 nm)/Pyrimidine compound F-2 (30 nm)/Alq$_3$ (20 nm)/LiF (0.5 nm)/Al (150 nm).

Figure 15A:
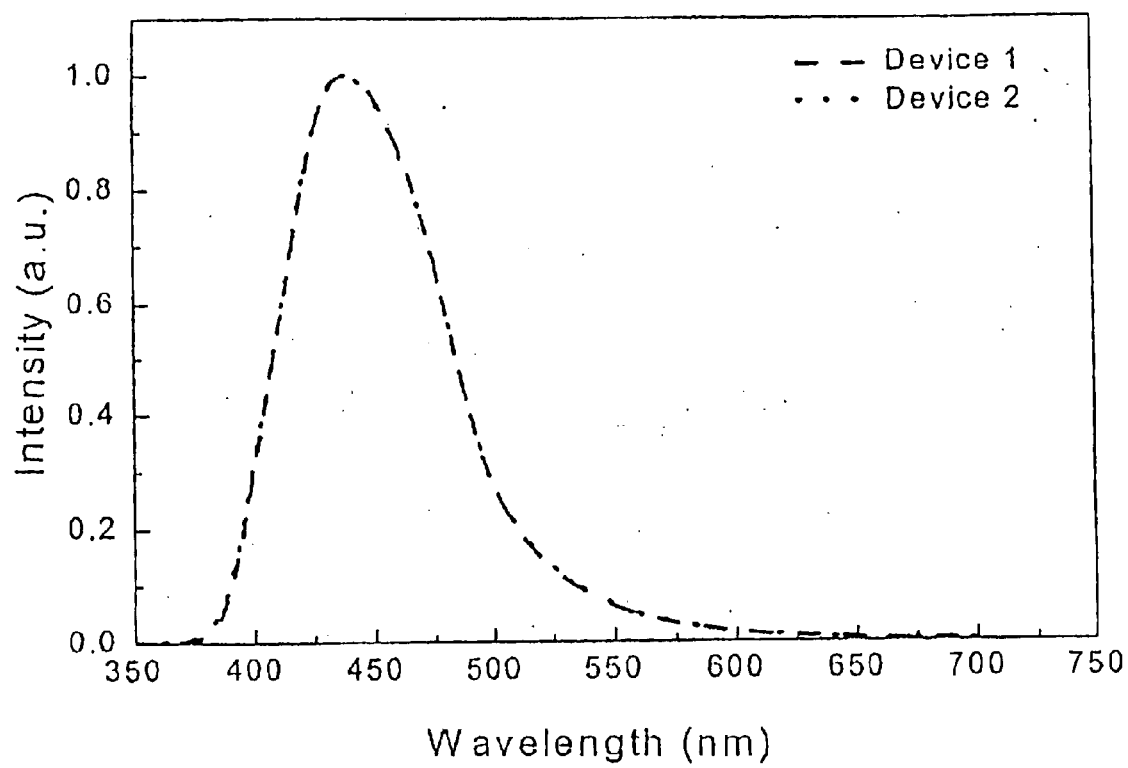
FIGS. 15a and 15b show a view of light-emitting characteristic with a Current-Voltage-Brightness curve of an OLED of a sixth preferred embodiment of the present invention.
Figure 15B:
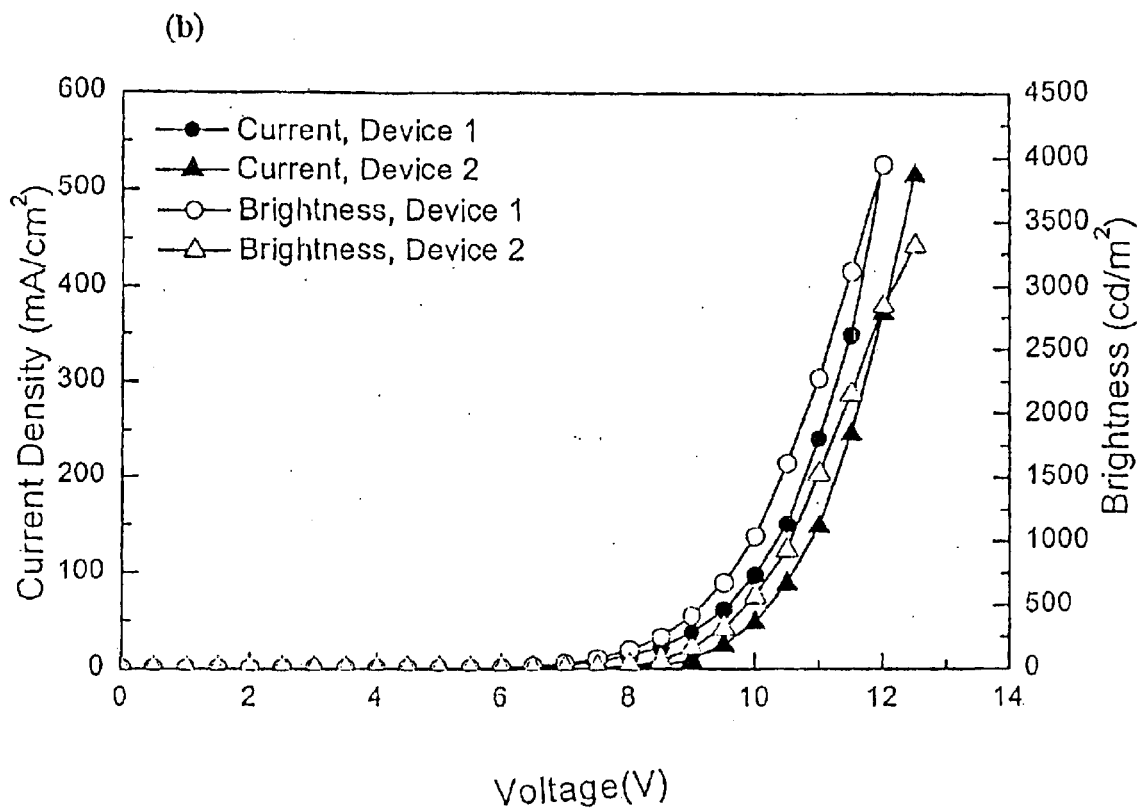

FIGS. 15a and 15b show a view of light-emitting characteristic with a Current-Voltage-B rightness curve of an OLED of a sixth preferred embodiment of the present invention.

As illustrated, the light-emitting characteristic demonstrates blue light emission of the fluorene-based pyrimidine-containing conjugated oligomer and it can be confirmed that the fluorene-based pyrimidine-containing conjugated oligomer does provide the function of blocking the holes transport in an OLED.

Each of those fluorene-based pyrimidine-containing conjugated oligomers when applied as the host blocking hole transport layer provides comparatively high brightness (>4000 cd/m$^2$ in case of Device 1; and 3500 cd/m$^2$, Device 2) while allowing the ~2.0% maximal external electroluminescent quantum efficiency for both devices.

In the sixth preferred embodiment of the present invention, the dopants free NCB is used as the light emitting layer; howsoever, anyone who is familiar with the art of OLED knows that if a highly efficient light emissive dopant is used, the light-emitting layer is capable of upgrading the light-emitting efficiency and regulating the light emissive color. Anyone who is familiar with the art of OLED should also know that the fluorene-based pyrimidine-containing conjugated oligomer is capable of being used in various types of structure of OLEDs as the hole blocking layer or a part of it.

What is claimed is:

1. A fluorene-based pyrimidine-containing conjugated oligomer used in an organic light-emitting device is described with its chemical formula as follows:

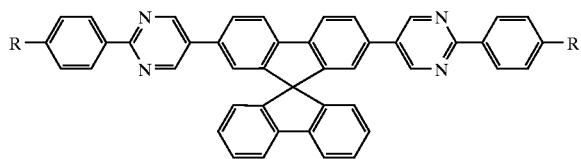

wherein R represents a 4-n-butyoxy group.

2. An organic light-emitting device comprising an electron transport layer containing the fluorene-based pyrimidine-containing conjugated oligomer as recited in claim 1.

3. An organic light-emitting device comprising an emitting layer containing the fluorene-based pyrimidine-containing conjugated oligomer as recited in claim 1.

4. An organic light-emitting device comprising a hole blocking layer containing the fluorene-based pyrimidine-containing conjugated oligomer as recited in claim 1.

5. A fluorene-based pyrimidine-containing conjugated oligomer used in an organic light-emitting device is described with its chemical formula as follows:

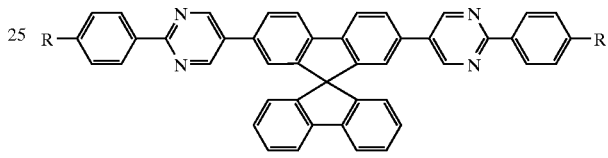

wherein R represents a 4-methoxyl group.

6. An organic light-emitting device comprising an electron transport layer containing the fluorene-based pyrimidine-containing conjugated oligomer as recited in claim 5.

7. An organic light-emitting device comprising an emitting layer containing the fluorene-based pyrimidine-containing conjugated oligomer as recited in claim 5.

8. An organic light-emitting device comprising a hole blocking layer containing the fluorene-based pyrimidine-containing conjugated oligomer as recited in claim 5.

9. A fluorene-based pyrimidine-containing conjugated oligomer used in an organic light-emitting device is described with its chemical formula as follows:

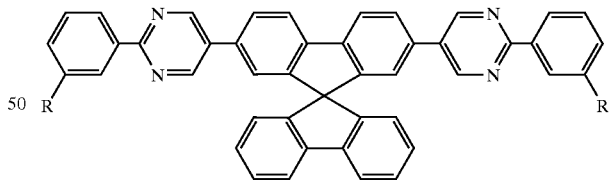

wherein R represents a 3-methoxyl group.

10. An organic light-emitting device comprising an electron transport layer containing the fluorene-based pyrimidine-containing conjugated oligomer as recited in claim 9.

11. An organic light-emitting device comprising an emitting layer containing the fluorene-based pyrimidine-containing conjugated oligomer as recited in claim 9.

12. An organic light-emitting device comprising a hole blocking layer containing the fluorene-based pyrimidine-containing conjugated oligomer as recited in claim 9.

* * * * *